US008696899B2

(12) United States Patent
Roulin et al.

(10) Patent No.: US 8,696,899 B2
(45) Date of Patent: Apr. 15, 2014

(54) DISPENSER FOR PREPARING A NUTRITIONAL COMPOSITION

(75) Inventors: Anne Roulin, Yverdon-les-Bains (CH); Yann Epars, Penthalaz (CH); Vincent Martin, Crissier (CH); Matthew Steven, Konolfingen (CN)

(73) Assignee: Nestec S.A., Vevey (CH)

( * ) Notice: Subject to any disclaimer, the term of this patent is extended or adjusted under 35 U.S.C. 154(b) by 702 days.

(21) Appl. No.: 12/375,084

(22) PCT Filed: Jul. 25, 2007

(86) PCT No.: PCT/EP2007/057636
§ 371 (c)(1),
(2), (4) Date: Jan. 26, 2009

(87) PCT Pub. No.: WO2008/012314
PCT Pub. Date: Jan. 31, 2008

(65) Prior Publication Data
US 2010/0021604 A1    Jan. 28, 2010

(30) Foreign Application Priority Data

Jul. 25, 2006 (EP) .................................... 06117801

(51) Int. Cl.
*A47J 31/40*    (2006.01)
*A23L 1/20*    (2006.01)

(52) U.S. Cl.
USPC ................. 210/184; 99/279; 99/281; 99/288; 99/291; 99/305; 99/302 R; 99/323.3; 210/500.21; 426/78; 426/84; 426/425; 426/432; 426/433

(58) Field of Classification Search
CPC ........... A47J 31/10; A47J 31/12; A47J 31/16; A47J 31/404; A47J 31/405; A47J 31/407; A47J 31/4489; A47J 31/56; A47J 31/605; A47J 31/60
USPC ............... 210/184; 222/146.2, 146.5, 189.06, 222/423, 542, 544, 566; 99/323.3
See application file for complete search history.

(56) References Cited

U.S. PATENT DOCUMENTS 2,824,676 A * 2/1958 Still et al. ...................... 222/442
3,927,974 A   12/1975 Johansson et al.
(Continued)

FOREIGN PATENT DOCUMENTS

DE        19618319      11/1997
DE        102005015129  10/2006
(Continued)

OTHER PUBLICATIONS

International Search Report for International Application No. PCT/EP2007/057636 mailed Oct. 16, 2007.
(Continued)

*Primary Examiner* — Krishnan S Menon
*Assistant Examiner* — Allison Fitzsimmons
(74) *Attorney, Agent, or Firm* — K&L Gates LLP

(57) ABSTRACT

A dispenser for a nutritional composition comprises a water reservoir, water heating means, water discharge means, a bacterial filter between the water heating means and the water discharge means such that heated water passes though the filter prior to discharge from the dispenser, and means to heat surfaces of the dispenser which come into contact with filtered water.

18 Claims, 5 Drawing Sheets

(56) References Cited

U.S. PATENT DOCUMENTS

| | | | |
|---|---|---|---|
| 4,581,239 A | | 4/1986 | Woolman et al. |
| 4,644,855 A | * | 2/1987 | Woolman et al. ............... 99/280 |
| 5,032,265 A | | 7/1991 | Jha et al. |
| 5,393,548 A | * | 2/1995 | Heiligman .................... 426/433 |
| 5,868,924 A | * | 2/1999 | Nachtman et al. .............. 210/85 |
| 6,517,880 B2 | * | 2/2003 | Walters et al. ................ 426/433 |
| 6,841,068 B1 | * | 1/2005 | Yoon et al. .................... 210/266 |
| 2002/0127005 A1 | * | 9/2002 | Roberson ...................... 392/442 |
| 2005/0178799 A1 | | 8/2005 | Cheong |
| 2006/0249030 A1 | * | 11/2006 | Bienvenu et al. ............... 99/291 |
| 2007/0110824 A1 | * | 5/2007 | Nageswaran ................. 424/604 |
| 2008/0041236 A1 | * | 2/2008 | Raouf et al. ................. 99/323.3 |

FOREIGN PATENT DOCUMENTS

| | | |
|---|---|---|
| EP | 1027835 | 8/2000 |
| GB | 2368621 | 5/2002 |
| TW | 450116 | 8/2001 |
| WO | WO 0156613 | 8/2001 |
| WO | WO 03059778 | 7/2003 |
| WO | WO 03084377 | 10/2003 |
| WO | WO 2004107940 | 12/2004 |
| WO | WO 2005068349 | 7/2005 |
| WO | WO 2005120313 | 12/2005 |
| WO | WO 2005120313 A1 * | 12/2005 |
| WO | WO 2006077259 | 7/2006 |
| WO | WO2008012314 | 1/2008 |

OTHER PUBLICATIONS

Written Opinion for International Application No. PCT/EP2007/057636 mailed Oct. 16, 2007.

Costerton et al. "Bacterial biofilms: a common cause of persistent infections" Science. May 21, 1999 284(5418), pp. 1318-1322.

* cited by examiner

DISPENSER FOR PREPARING A NUTRITIONAL COMPOSITION

The present invention relates to a dispenser for preparing a ready to drink nutritional composition such as an infant formula.

THE BACKGROUND ART

Mother's milk is recommended for all infants. However, in some cases breast feeding is inadequate or unsuccessful or inadvisable for medical reasons or the mother chooses not to breast feed. Infant formulas have been developed for these situations.

Generally infant formulas are available in powder form, concentrated liquid form, or ready to feed liquid form. Powdered infant formulas are the most popular form; primarily due to their cost and nutritional quality. The key disadvantage with powdered infant formulas is the inconvenience of preparation. The powdered formula must be spooned into a sterilised drinking vessel such as a baby bottle, water which has been boiled and allowed to cool is poured into the drinking vessel to reconstitute the formula and the drinking vessel is then sealed and shaken to ensure the powder has been dissolved. It may be noted that milk-based nutritional compositions such as infant formula provide excellent substrates for bacterial growth. Therefore, to avoid any bacterial growth, the formula should be consumed immediately after reconstitution.

If prepared and consumed in this manner, powdered infant formulas provide a safe and nutritionally good substitute for mother's milk in the situations described above. However, the process needs to be repeated every time a feed is required. It may readily be seen that this may not always be convenient and, as a consequence, many parents and other caregivers do not prepare the formulas properly and hence expose the infant to the risk of infection. For example, the water may not be boiled prior to use in which case any pathogens in the water are fed to the infant. Usually water sources in developed countries are reasonably safe but this may not be the case everywhere. Alternatively, batches of the infant formula may be prepared and then stored until needed. Unfortunately, if any pathogen has contaminated the formula, it then has time to replicate.

Infant formulas in concentrated liquid form suffer substantially the same disadvantages as powdered infant formulas. Hence they do not provide a better solution. Infant formulas in ready to feed form should in theory provide a solution to the inconvenience of preparation. However, they have their own disadvantages; in particular they are much more costly and bulky. Further, it is often necessary to provide them in a size enabling multiple feeds. However once opened for the first feed, a contamination risk remains.

Similar issues arise with other nutritional compositions for children such as growing up milks and infant cereals, and for nutritional compositions for adults such as feeds used in health care environments.

In view of these concerns and with the intention of providing liquid nutritional compositions such as infant formula in a convenient and safe manner, various devices for the preparation of individual servings of such compositions have already been proposed. For example WO 2004/107940 proposes a device having a first water chamber in which water to be used in the reconstitution of the composition is boiled then transferred to a second chamber in which it is held until required at which point it is reheated to the desired temperature of administration and dispensed into a baby bottle where it is mixed with powdered infant formula to prepare a single feed in the conventional way. Alternatively, the powdered infant formula and reheated water may be mixed together before being dispensed into the bottle. WO 03/084377 proposes a device comprising a sterilisation unit, a container and dispenser for the powdered infant formula, a water reservoir and a water pump all linked to a controller such as a microprocessor. This device would sterilise baby bottles, dispense the desired amount of infant formula into the sterilised bottle, pre-boil the water and then maintain it at a suitable temperature, and finally dispense the desired amount of water at the desired temperature into the bottle to reconstitute the infant formula.

These known devices are mainly directed towards providing single servings of infant formula in a convenient manner. However, the immune defences of infants and young children are generally not fully developed and, as a result, these populations are particularly vulnerable to both bacterial and viral infections. For example, they may be prone to infections in circumstances where the immune system of a healthy adult would resist infection or they may suffer more serious consequences as a result of infection than would a healthy adult.

Similar difficulties may arise in populations where the immune system is compromised such as the elderly. The consequence of this is that dispensing devices that produce products which are perfectly safe for healthy adults may not be able to produce products which meet the increased safety standards required for products to be consumed by subjects having immature or compromised immune systems. Dispensing equipment may provide a more convenient way to prepare single servings of nutritional compositions such as infant formula but its use brings new problems that are not encountered using traditional methods. This is not simply a question of sterilising the water which will be used to reconstitute the composition, attention must also be paid to such questions as the possibilities of bio-adhesion and build-up of biofilms within the equipment itself and the consequences of adhering bacteria or biofilms detaching and contaminating the previously sterilised water.

It has been observed that such biofilms may be formed within dispensing equipment even if the water dispensed therefrom has previously been boiled. It is thought that this may occur because it is very difficult to ensure that such previously boiled water remains sterile as this would entail a complete separation from the atmosphere. Once the water is again contaminated by bacteria at however low a level, it is possible that, over time, bio-adhesion will occur and biofilms will grow and adhere to surfaces with which the water is in contact, particularly in corners and crevices. Thus, although the microbial content of the water itself may be perfectly satisfactory for the preparation of infant formula, the recontamination of the water with bacteria from the atmosphere nevertheless allows biofilms to grow within the dispensing equipment parts of which films may detach and contaminate water dispensed from the equipment at a later stage.

Once a biofilm has formed, it is almost impossible to remove it completely. It may be possible to kill most of the bacteria in the film but the film itself is difficult to dislodge and can then serve as a substrate and nutrient for any live bacteria remaining or newly arriving to recolonise the surface in question.

In order that the scale of this challenge may be understood, it may be noted that the maximum microbial count recommended by Swiss legislation for products dispensed from vending machines is 100000 colony forming units (cfu) per ml whereas the maximum recommended count for infant formula is around 100 cfu/ml.

Therefore, although it is clear that use of dispensing equipment can greatly facilitate ease of preparation of nutritional compositions such as infant formulas, such use brings with it new safety concerns. There is, therefore, clearly a need to provide dispensers for such products with improved safety features.

SUMMARY OF THE INVENTION

Accordingly the present invention provides a dispenser for a nutritional composition comprising a water reservoir, water heating means, water discharge means, a bacterial filter between the water heating means and the water discharge means such that, in use, heated water passes though the filter prior to discharge from the dispenser, and means to heat surfaces of the dispenser which, in use, will come into contact with filtered water.

The invention extends to a method of dispensing infant formula comprising heating water to a temperature between 25 and 45° C., passing the heated water through a bacterial filter, mixing the filtered water with the infant formula in the form of a powder or a concentrated liquid and dispensing the liquid infant formula.

DETAILED DESCRIPTION OF THE INVENTION

Figure 1:
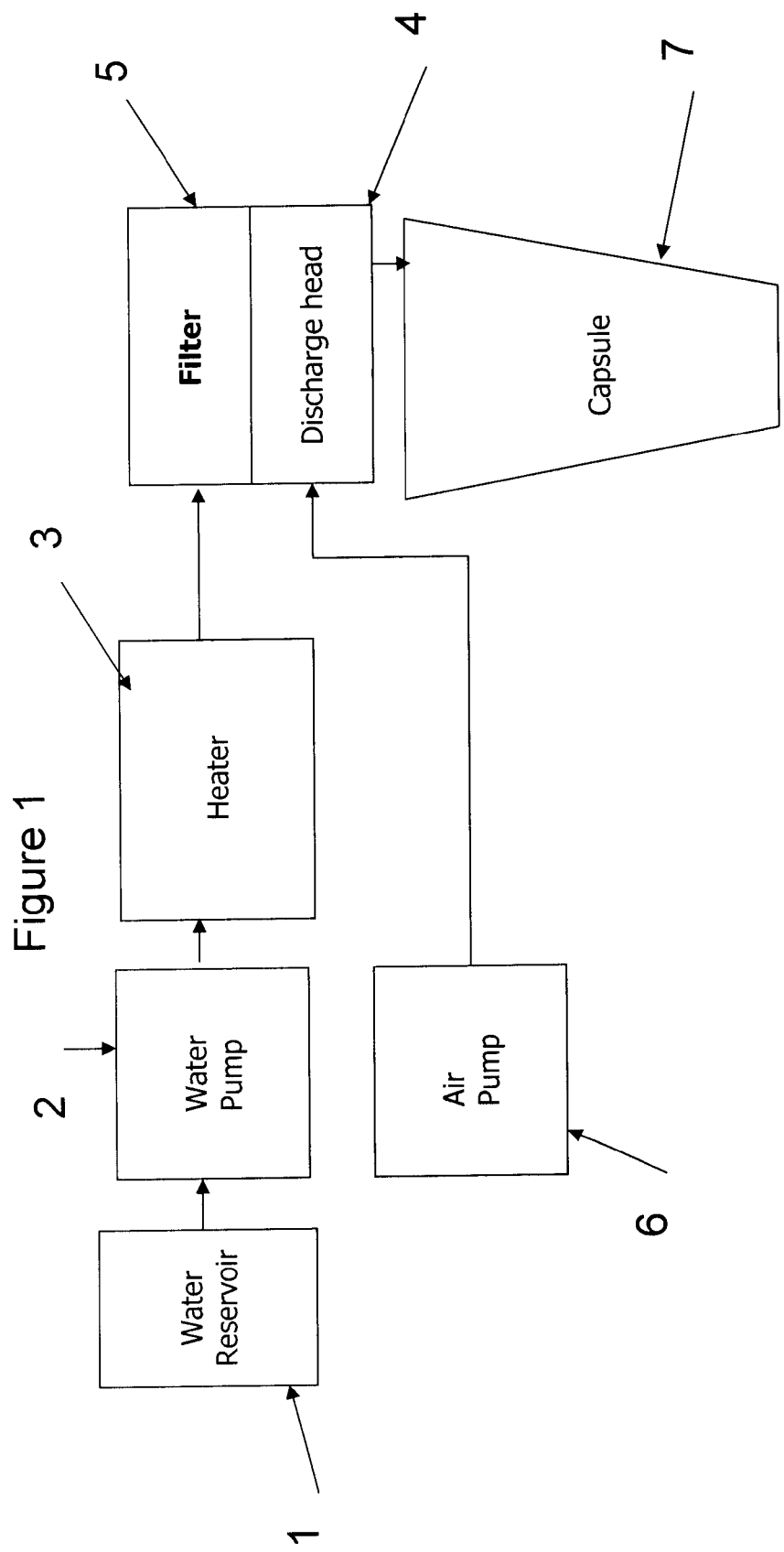
FIG. 1 shows schematically one embodiment of a dispenser according to the invention.

In this specification, the following terms have the following meanings:—
"bio-adhesion" means bacteria adhering to an inert surface;
"biofilm" means a structured community of bacterial cells enclosed in a self-produced polymeric matrix and adherent to an inert surface and is a specialised case of bio-adhesion (after Costerton et al, "Bacterial Biofilms: A Common Cause of Persistent Infections", Science, Vol 284, pages 1318-1322);
"bacterial filter" means a filter which is capable of physically obstructing the passage of bacteria in water flowing through it.

The present invention is primarily directed to minimising any hazard presented by bio-adhesion and/or the formation of biofilms within dispensing equipment to be used in the preparation of infant formula or other nutritional compositions intended for consumption by subjects with an immature or compromised immune system.

This object is achieved by including within the dispensing equipment a bacterial filter and means for heating surfaces of the dispenser that will come into contact with filtered water. The filter acts as a physical barrier to prevent the passage of any bacteria present in the water whether naturally (i.e. present in the mains water supply or mineral water) or as the result of detachment of a biofilm or other colony of adherent bacteria within the fluid system (the water reservoir or the pipes for example).

The risk of contamination by biofilms is further reduced by separately providing heating means to reduce the adhesion and proliferation of bacteria and the formation of biofilms in regions of the water discharge means downstream of the filter. For example, surfaces of the dispenser with which filtered water will be in contact may be provided with heating means operable to directly heat the surfaces as often as necessary to prevent bio-adhesion and/or formation of biofilms on these surfaces. Alternatively or additionally, means may be provided to regularly clean the bacterial filter and the water discharge means to discourage the adhesion and proliferation of bacteria and formation of biofilms in this area by the application of heat to these surfaces. For example, a steam generator may be provided such that the interior of the water discharge means and preferably the bacterial filter as well may be cleaned by the passage of steam.

It will be seen that use of a dispenser according to the invention removes the need for the water to be boiled prior to use as the filter by itself will purify the water to the required standard. This in turn enables the design of the dispenser to be simplified if desired.

The bacterial filter may have a nominal pore size of 0.45 microns or less. A particularly preferred nominal pore size is between 0.1 and 0.2 microns. The bacterial filter may be a conventional flat membrane filter or a shaped filter such as a hollow ceramic cylinder wherein the filtration layer is coated onto either the interior or exterior surface of the cylinder and water percolates from the inside the cylinder out or from outside the filter in, accordingly. One example of a suitable material is the ceramic filter pipes (mono-channel and multi-channel) sold by atech innovations GmbH and ItN Nanovation AG. Alternatively, the filter may be composed of fibres which themselves have a structure which acts as a bacterial filter. One example of a suitable material is the hollow fibres manufactured by Gambro Dialysatoren GmbH for the Hemofilter 2×.

Preferably, the bacterial filter is located close to the water discharge means.

As noted above, heating means are provided to reduce the adhesion and proliferation of bacteria and the formation of biofilms in regions of the water discharge means downstream of the bacterial filter. Preferably, such heating means are provided by a steam generator arranged to deliver steam to at least those internal surfaces downstream of the bacterial filter that will be contacted by filtered water when the dispenser is in use. More preferably, steam is also delivered to the bacterial filter itself. The internal surfaces downstream of the water filter may be made from a material which discourages adhesion and/or proliferation of bacteria such as Teflon®, a bacteriostatic material or stainless steel.

A complete cycle of operation of the dispenser may comprise the following steps:—
1. Steam is supplied from the steam generator to the water discharge means for a period of 20 seconds to sanitise the internal surfaces of the water discharge means downstream of the bacterial filter;
2. Then the desired quantity of water passes from the water reservoir to the water heating means where it is heated to the desired discharge temperature (preferably between 25 and 45° C.);
3. The heated water passes through the bacterial filter to the sanitised water discharge means and is dispensed as required.

In this case, two heating means may be required, one to generate steam and one to heat the water to be dispensed.

Alternatively, the steam-cleaning could be performed at the end of the operating cycle in which case the sequence would be as follows:—
1. The desired quantity of water passes from the water reservoir to the water heating means where it is heated to the desired discharge temperature (preferably between 25 and 45° C.);
2. The heated water passes through the bacterial filter to the water discharge means and is dispensed as required;
3. Steam is supplied from the steam generator to the water discharge means for a period of 20 seconds to sanitise the internal surfaces of the water discharge means downstream of the bacterial filter.

In this case, the same heating means could be used to heat the water to be dispensed and to generate the steam. Preferably, however, two heating means are provided as outlined above.

A dispenser according to the invention may also be equipped with other features to make the process of preparing individual servings of nutritional compositions even more convenient. For example, the dispenser may include a steriliser for baby bottles or the like containers and/or a water pump if it is desired to operate the dispenser under pressure.

A dispenser according to the invention is particularly suitable for use with individually packaged unit doses of the nutritional composition to be prepared. Such a concept is described in more detail in our co-pending patent application published under International Publication Number WO 2006/077259, the contents of which are incorporated herein by reference. Briefly, the water discharge means is adapted to receive a sealed disposable capsule containing a unit dose of the composition in concentrated form. The capsule has an outlet which opens in response to pressure of water within the capsule so that when the dispenser is operated to introduce water into the capsule and the required pressure is attained within the capsule it opens to allow the nutritional composition to flow directly from the capsule outlet into a drinking vessel without contacting the dispenser.

The nutritional composition is preferably present in the capsule in powder form but may alternatively be in the form of a concentrated liquid.

The dispenser may further be provided with means to flush the capsule with a gas after introduction of the water to empty the capsule of liquid and to restrict any flow back of the nutritional composition into the dispenser. A suitable gas is air at a pressure of between 200 mbar and 2 bar, for example 300 mbar.

The capsule may be configured to suit the dispenser provided always that the configuration is such as to enable opening of the capsule in such a way as to allow liquid to drain directly from the capsule into the receiving vessel and that the means for opening the capsule to allow liquid to drain from it is located within the capsule itself and is operable in response to conditions generated in the capsule by the introduction of water into the capsule. Various suitable capsule configurations of this type are disclosed in our co-pending patent application published under International Publication Number WO 03/059778, the contents of which are incorporated herein by reference.

As will be appreciated by those skilled in the art, the dispenser will also include control means and appropriate circuitry to enable it to be operated as desired.

For example, in the case of preparation of infant formula, the delivery of the water is preferably arranged such that the temperature of the final product in the receiving vessel is at a suitable temperature for the infant to drink immediately, for example between 25 and 45° C. This may be achieved by simply programming the water heating means to heat the water to the desired temperature as selected by the consumer. Alternatively, 30 to 50% of the water may be discharged at a temperature of between 70 and 80° C. and then the remaining amount at or about room temperature or the water at room temperature may be discharged first followed by the hot water. In both cases the mixture of hot water with water at room temperature will ensure that the resulting ready to drink infant formula is at a temperature suitable for immediate consumption For other nutritional products targeted, for example, at adults with a compromised immune system and/or elderly people a higher temperature could be selected.

Similarly, the control means preferably includes means to regulate the amount of water to be discharged. This may be selected manually by the operator. Alternatively, if unit dose capsules are to be used, the capsules may be provided with a bar code which is read by a sensor provided on the dispenser and adapted to pass a signal to the control means to trigger the heating and discharge of the correct amount of water.

The invention will now be further illustrated by reference to the drawings.

FIG. 1 shows schematically one embodiment of a dispenser according to the invention. The dispenser consists of a water reservoir 1 provided with a water pump 2 to pass water to heater 3 which comprises a coiled stainless-steel pipe in a die cast aluminium thermoblock (not shown). Power is supplied to the thermoblock sufficient to heat the water to the desired temperature as it passes though the pipe. From heater 3, water is supplied to a discharge head 4 provided with a bacterial filter 5 comprising two superposed hydrophilic PES (polyethersulphone) membranes, the upper layer having a pore size of 0.8 microns and the lower layer having a pore size of 0.2 microns (EKV filter with nominal pore size of 0.2 microns supplied by Pall Corporation). Means (not shown) are provided to heat the internal surfaces of the discharge head 4 downstream of the filter 5. An air pump 6 is also connected to discharge head 4. In operation, the heating means is first operated to heat the internal surfaces of the discharge head downstream of the filter to sanitise them. Then, the desired quantity of water is pumped at a pressure of about 0.2 bar from reservoir 1 to heater 3 where it is heated to a temperature between 25 and 40° C. The heated water is passed through bacterial filter 5 to discharge head 4 at a pressure of between 2 and 7 bar and dispensed from there into a capsule 7 which contains a unit dose of a nutritional composition such as an infant formula. When the pressure in capsule 7 reaches a predetermined value, the capsule opens and the reconstituted infant formula is dispensed directly from the capsule into a suitable receptacle such as a baby bottle (not shown). Air pump 6 is then operated to flush any remaining liquid out of the capsule and into the receptacle.

Figure 2:
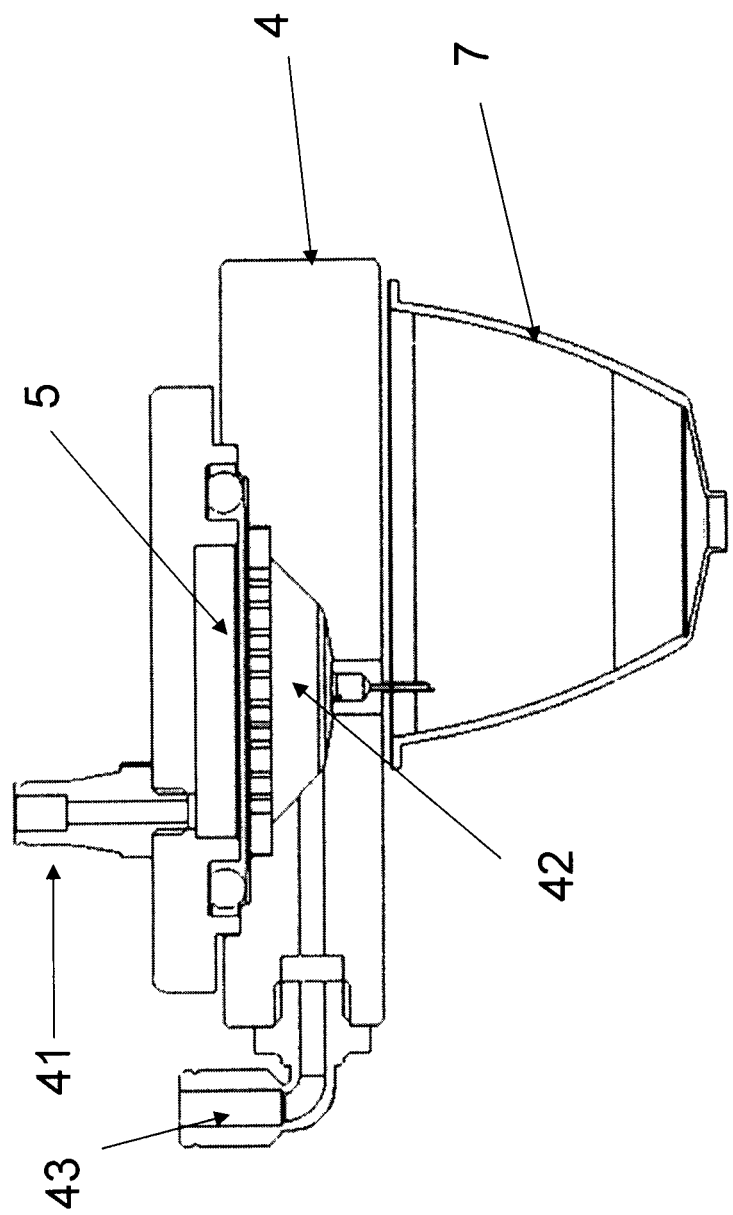
FIG. 2 shows a cross-section through the water discharge means of the embodiment of FIG. 1

FIG. 2 shows a cross section through an embodiment of discharge head 4 in which the filter 5 is incorporated in the discharge head. Heated water is supplied from heater 3 and enters the top of the discharge head through inlet 41. The heated water then passes through the filter 5 and into chamber 42 before passing to capsule 7. It may be seen that chamber 42 is also connected to air pump 6 (not shown in FIG. 2) via inlet 43.

Figure 3:
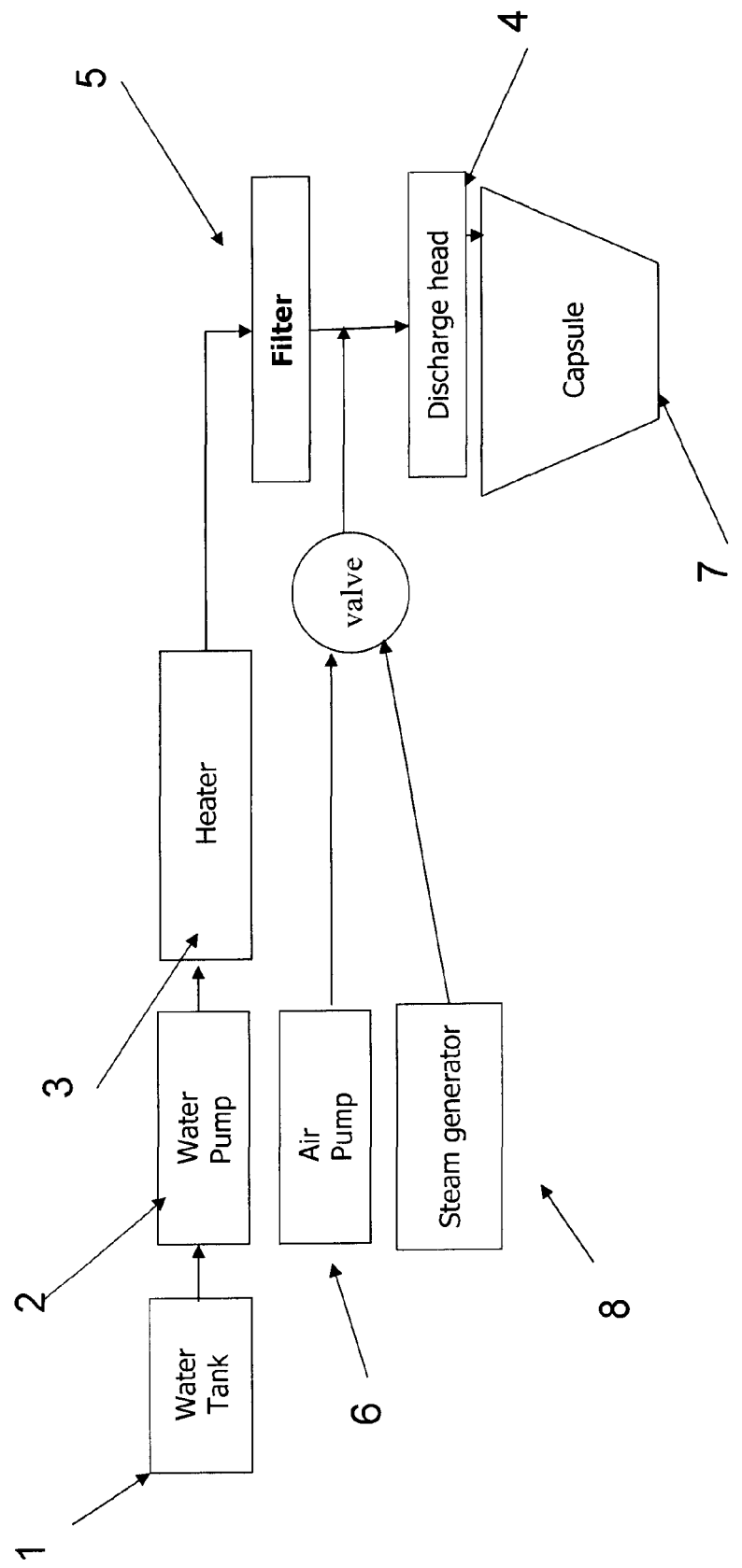
FIG. 3 shows schematically another embodiment of a dispenser according to the invention.

FIG. 3 shows schematically another embodiment of a dispenser according to the invention. As may be seen from FIG. 3, this is similar to the embodiment of FIG. 1 but is provided with a steam generator 8 connected to the discharge head 4 in place of the heating means. In operation, the interior of discharge head, the filter and, in particular chamber 42 (FIG. 2) may be sterilised as often as desired by passing steam from the steam generator through the discharge head.

Figure 4:
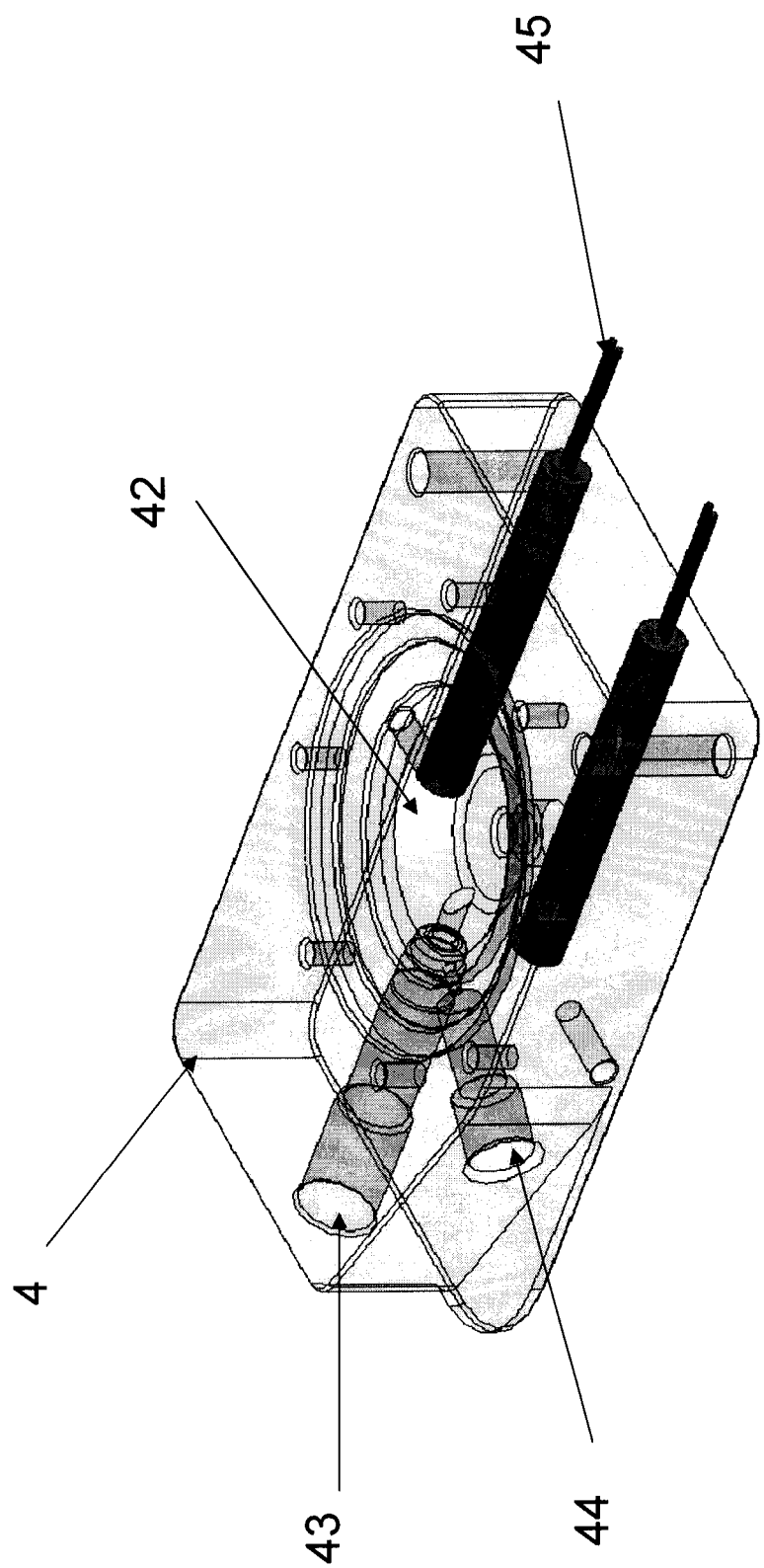
FIG. 4 shows in perspective an embodiment of water discharge means for use in a dispenser according to the invention.

FIG. 4 shows an alternative embodiment of the discharge head 4 of the embodiment of FIG. 3. As may be seen from this figure, in addition to the water inlet 43 and a steam inlet 44, the discharge head is provided with electrical heating elements 45 whereby the discharge head may be heated during operation of the dispenser to further discourage the adhesion and proliferation of bacteria in chamber 42.

Figure 5A:
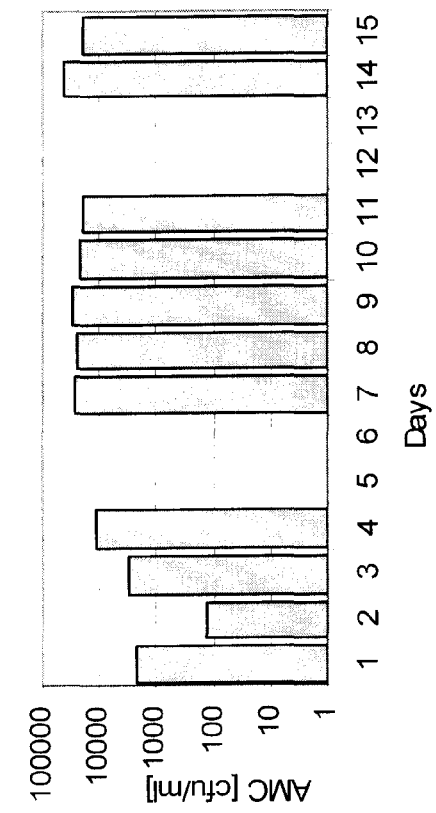
FIG. 5 compares the microbial count in infant formula dispensed from a dispenser according to the invention with that obtained from conventional dispensers.
Figure 5B:
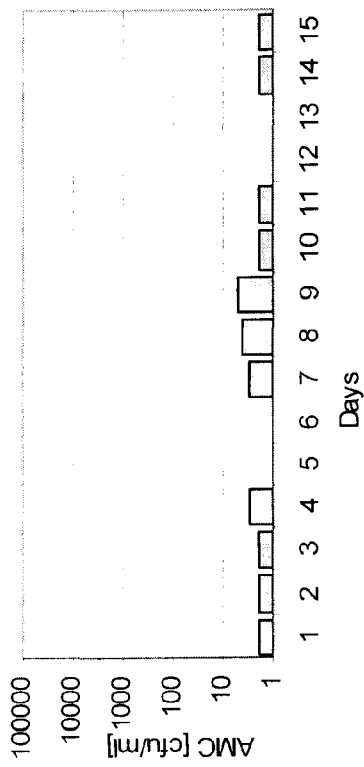
Figure 5C:
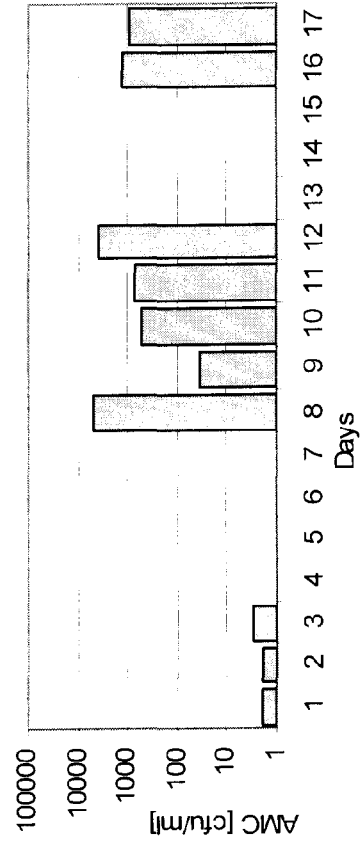

Finally, FIG. 5 compares the bacterial contamination in infant formula discharged from a dispenser according to the invention (FIG. 5a) with the bacterial contamination in infant formula discharged from a similar dispenser without a bacterial filter (FIG. 5b) and with the bacterial contamination in infant formula discharged from a dispenser such as that disclosed in WO 03/084377 in which the water is pre-boiled and the dispenser is flushed with 45 ml of boiling water every two days (FIG. 5c). In each case, the test period was two weeks.

The machines were operated as they would be in a family having one infant i.e. six servings per day were prepared using each dispenser with the servings being prepared at spaced intervals. In each case, the sample analysed was the first serving to be discharged by the dispenser on the day in question as this is likely to be the worst sample because water has been stagnating in the machine overnight. The total aerobic mesophilic content (AMC) was then determined for each sample and the results are shown in FIG. 5a for a dispenser according to the invention, FIG. 5b for the conventional dispenser and FIG. 5c for the prior art dispenser. AMC was determined by incubating each sample at ambient temperature and exposed to the air until the bacterial colonies were large enough to be measured. From FIG. 5a it may be seen that the AMC of samples discharged from a dispenser according to the invention was in all case below 10 cfu/ml. From a comparison of FIG. 5a with FIGS. 5b and 5c, it may be seen that the AMC of samples discharged from the conventional dispensers exceeded $10^3$ cfu/ml i.e. was at least 2 orders of magnitude higher. From FIG. 5c in particular it appears that, contrary to what might be expected, even cleaning by flushing with boiling water as described above cannot prevent colonisation of the pipes and other internal surfaces by bacteria and the subsequent contamination of the previously boiled water used to prepare the infant formula.

The invention clamied is:

1. A dispenser for a nutritional composition comprising:
a water reservoir,
a water heater that heats water to a temperature between 25 and 45° C.,
a water pump,
a water discharge device that receives a sealed disposable capsule containing a unit dose of infant formula in a form of powder or a concentrated liquid,
a bacterial filter between the water heater and the water discharge device so that the heated water passes through the filter prior to discharge from the dispenser, the water pump passes the heated water through the bacterial filter for mixing the filtered water with the infant formula to form a reconstituted infant formula and dispensing the reconstituted infant formula,
means to heat surfaces of the dispenser which, in use, will come into contact with filtered water, the means to heat the surfaces provided separately from the water heater and comprising a steam generator that delivers steam to, at least, the internal surfaces downstream of the bacterial filter to clean the bacterial filter and reduce adhesion and proliferation of bacteria and formation of biofilm in the water discharge device downstream of the bacterial filter, and
control means that operate steam delivery from the steam generator for cleaning and reducing the adhesion and the proliferation of bacteria and the formation of biofilm, operate water heating by the water heater, and operate the water pump for dispensing the liquid infant formula.

2. The dispenser of claim 1, wherein the filter is a flat membrane filter.

3. The dispenser of claim 1, wherein the filter is located adjacent to the water discharge device so that the heated water passes though the filter prior to the discharge device.

4. The dispenser of claim 1, wherein the bacterial filter has a nominal pore size of 0.45 microns or less.

5. The dispenser of claim 1, wherein the bacterial filter has a nominal pore size between 0.1 and 0.2 microns.

6. The dispenser of claim 1, wherein the filter is directly connected to the water discharge device.

7. The dispenser of claim 1, wherein the steam generator delivers the steam to all surfaces of the water discharge device downstream of the filter that will come into contact with filtered water when the dispenser is in use.

8. The dispenser of claim 1 comprising a steriliser for baby bottles.

9. The dispenser of claim 1, wherein the steam generator is connected to an interior of the water discharge device.

10. The dispenser of claim 1 comprising an air pump connected to the water discharge device and the chamber and operable so as to flush the capsule with air after introduction of water into the capsule so as to empty the capsule of liquid and prevent back flow of liquid into the dispenser.

11. A dispenser for a nutritional composition comprising:
a water reservoir,
a water heater that heats water to a temperature between 25 and 45° C.,
a water pump,
a water discharge device that receives a sealed disposable capsule containing a unit dose of infant formula in a form of powder or a concentrated liquid,
a bacterial filter between the water heater and the water discharge device so that the heated water passes through the filter prior to the discharge, the water pump passes the heated water through the bacterial filter for mixing the filtered water with the infant formula to form a reconstituted infant formula and dispensing the reconstituted infant formula,
a steam generator that is separate from the water heater and delivers a steam to, at least, the internal surfaces downstream of the bacterial filter to clean the bacterial filter and reduce adhesion and proliferation of bacteria and formation of biofilm in the water discharge device downstream of the bacterial filter, and
a controller that operates steam delivery from the steam generator for cleaning and reducing the adhesion and the proliferation of bacteria and the formation of biofilm, operates water heating by the water heater, and operates the water pump for dispensing the liquid infant formula.

12. A dispenser for a nutritional composition consisting of:
a water reservoir,
a water heater that heats water to a temperature between 25 and 45° C.,
a water pump,
a water discharge device that receives a sealed disposable capsule containing a unit dose of infant formula in a form of powder or a concentrated liquid, a bacterial filter between the water heater and the water discharge device so that the heated water passes though the filter prior to discharge from the dispenser, the water pump passes the heated water through the bacterial filter for mixing the filtered water with the infant formula to form a reconstituted infant formula and dispensing the reconstituted infant formula, means to heat surfaces of the dispenser which, in use, will come into contact with filtered water, the means to heat the surfaces provided separately from the water heater and comprising a steam generator that delivers steam to, at least, the internal surfaces downstream of the bacterial filter to clean the bacterial filter and reduce adhesion and proliferation of bacteria and formation of biofilm in the water discharge device downstream of the bacterial filter, and a controller that operates steam delivery from the steam generator for cleaning and reducing the adhesion and the proliferation of bacteria and the formation of biofilm, operates water heating by the water heater, and operates the water pump for dispensing the liquid infant formula.

13. The dispenser of claim 12, wherein the filter is a flat membrane filter.

14. The dispenser of claim 12, wherein the filter is located adjacent to the water discharge device so that the heated water passes though the filter prior to the discharge device.

15. The dispenser of claim 12, wherein the bacterial filter has a nominal pore size of 0.45 microns or less.

16. The dispenser of claim 12, wherein the bacterial filter has a nominal pore size between 0.1 and 0.2 microns.

17. The dispenser of claim 12, wherein the filter is directly connected to the water discharge device.

18. The dispenser of claim 12, wherein the steam generator delivers the steam to all surfaces of the water discharge device downstream of the filter that will come into contact with filtered water when the dispenser is in use.

* * * * *